(12) United States Patent
Cornish et al.

(10) Patent No.: US 6,589,253 B1
(45) Date of Patent: Jul. 8, 2003

(54) ULTRASONIC ANGIOPLASTY TRANSMISSION WIRE

(75) Inventors: Wayne E. Cornish, Fallbrook, CA (US); Douglas H. Gesswein, Temecula, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 09/475,780

(22) Filed: Dec. 30, 1999

(51) Int. Cl.[7] ............................................. A61B 17/225
(52) U.S. Cl. ............................................ 606/128; 601/2
(58) Field of Search .......................... 606/128, 127, 606/159, 169, 171; 604/22; 601/2

(56) References Cited

U.S. PATENT DOCUMENTS

| 4,721,117 A | 1/1988 | Mar et al. ................. 128/772 |
| 4,870,953 A | 10/1989 | DonMicheal et al. ......... 128/24 |
| 4,925,445 A | 5/1990 | Sakamoto et al. ........... 604/95 |
| 5,163,421 A | 11/1992 | Bernstein et al. ......... 128/24.1 |
| 5,267,954 A | 12/1993 | Nita ........................... 604/22 |
| 5,304,115 A | 4/1994 | Pflueger et al. ............. 604/22 |
| 5,365,943 A | 11/1994 | Jansen ....................... 128/772 |
| 5,368,557 A | 11/1994 | Nita et al. .................. 604/22 |
| 5,380,274 A | 1/1995 | Nita ........................... 604/22 |
| 5,397,293 A | 3/1995 | Alliger et al. ................ 601/2 |
| 5,411,476 A | 5/1995 | Abrams et al. .............. 604/95 |
| 5,427,118 A | 6/1995 | Nita et al. .................. 128/772 |
| 5,542,917 A | 8/1996 | Nita et al. .................. 604/22 |
| 5,606,979 A | 3/1997 | Hodgson .................... 128/772 |
| 5,735,811 A | 4/1998 | Brisken ....................... 604/22 |
| 5,827,201 A | 10/1998 | Samson et al. ............. 600/585 |
| 5,846,218 A | 12/1998 | Brisken et al. .............. 604/22 |
| 5,951,480 A * | 9/1999 | White et al. ............... 600/463 |
| 5,989,208 A | 11/1999 | Nita ............................ 604/22 |
| 6,007,514 A | 12/1999 | Nita ............................ 604/22 |
| 6,241,703 B1 * | 6/2001 | Levin et al. ................. 604/22 |
| 6,277,084 B1 * | 8/2001 | Abele et al. ................ 29/270 |
| 6,290,656 B1 | 9/2001 | Boyle et al. ............... 600/585 |
| 6,296,620 B1 | 10/2001 | Gesswein et al. ............ 605/22 |

* cited by examiner

Primary Examiner—Kevin Shaver
Assistant Examiner—Michael B. Priddy
(74) Attorney, Agent, or Firm—Fulwider Patton Lee & Utecht, LLP

(57) ABSTRACT

The ultrasonic angioplasty transmission wire for use in an ultrasonic angioplasty device comprises an inner layer of a first ultrasound transmitting material, and at least one outer coaxial shell or tube of a second ultrasound transmitting material different from the first ultrasound transmitting material. The first inner layer and one or more of the outer coaxial shells or tubes can be formed of ultrasound transmitting metal compositions such as stainless steel, nickel-titanium, or aluminum, or other similar suitable ultrasound transmitting metals. In one embodiment, the first inner layer is formed of a nickel-titanium alloy, and at least one outer coaxial shell or tube is formed of stainless steel. In another embodiment, the first inner layer is formed of nickel-titanium alloy, a first outer coaxial shell or tube is formed of stainless steel, and a second outer coaxial shell or tube is formed of the nickel-titanium alloy.

11 Claims, 3 Drawing Sheets

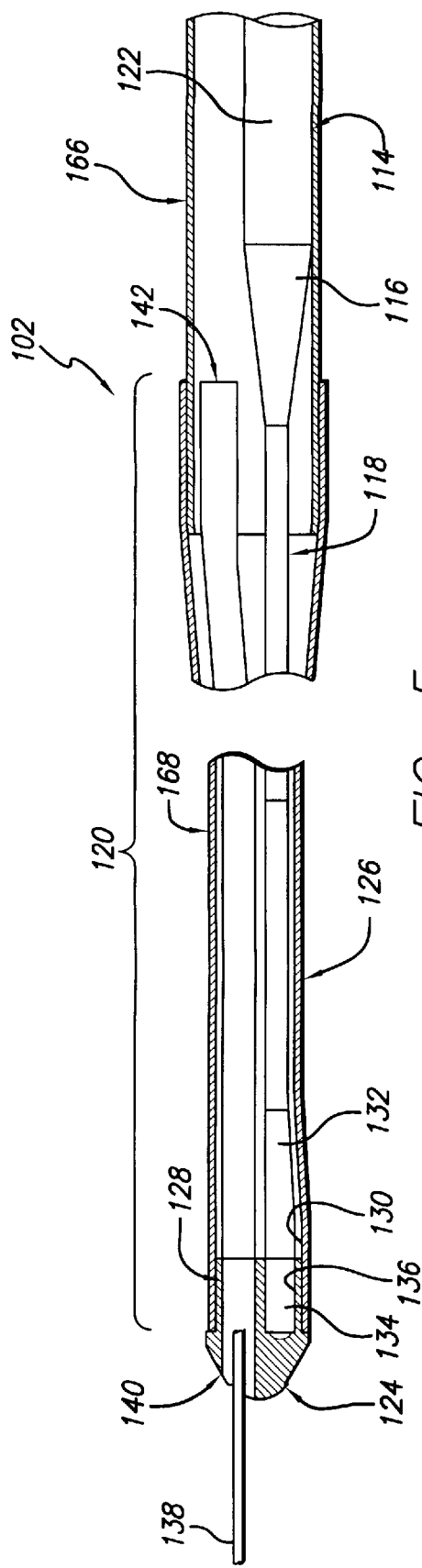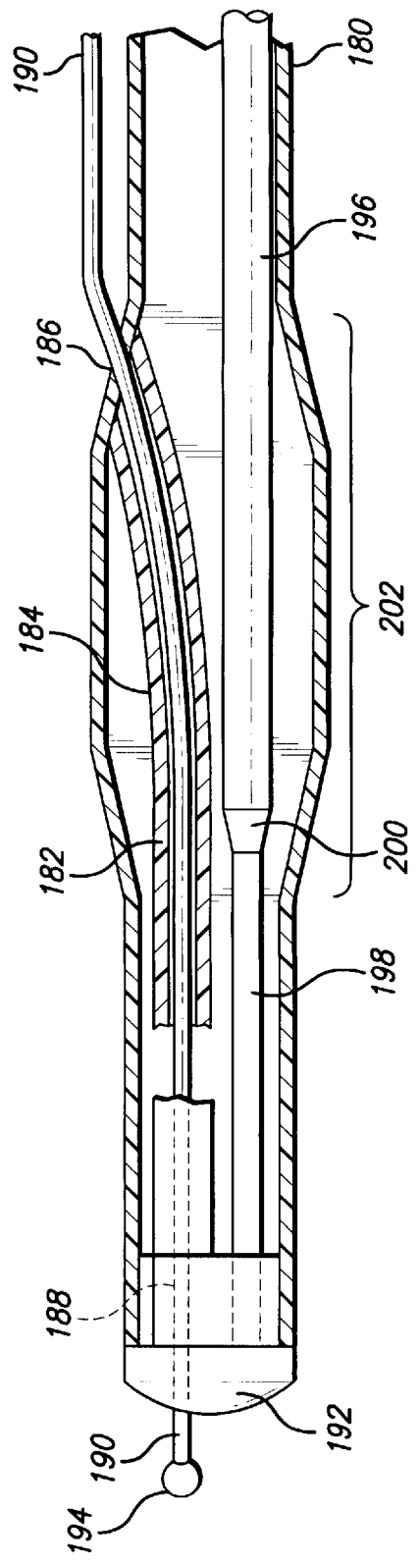

ULTRASONIC ANGIOPLASTY TRANSMISSION WIRE

BACKGROUND

This invention relates generally to medical devices, and more particularly concerns an improved ultrasound transmission member for use in an ultrasonic catheter for treatment of blockages of hollow anatomical structures.

In typical percutaneous transluminal coronary angioplasty (PTCA) procedures, a guiding catheter having a preformed distal tip is percutaneously introduced into the cardiovascular system of a patient through the brachial or femoral arteries and is advanced therein until the distal tip thereof is in the ostium of the desired coronary artery. A guide wire and a dilatation catheter having a balloon on the distal end thereof are introduced through the guiding catheter with the guide wire slidably disposed within an inner lumen of the dilatation catheter. The guide wire is first advanced into the patient's coronary vasculature until the distal end thereof crosses the lesion to be dilated and then the dilatation catheter is advanced over the previously introduced guide wire until the dilatation balloon is properly positioned across the lesion. The balloon may then be inflated to treat the lesion. Thereafter, a stent device may be located at the treated lesion, if deemed necessary.

In "ultrasonic" angioplasty, an ultrasonic angioplasty catheter is similarly advanced to an area of vascular blockage, and mechanical vibration at ultrasonic frequencies, generated typically by a piezoceramic transducer, is delivered along an ultrasonic angioplasty transmission member or wire to a distal catheter tip. When the distal catheter tip is abutted against intravascular blockage, the vibration of the distal end of the ultrasonic angioplasty transmission member removes the obstruction by mechanical impact and cavitation.

Ultrasonic angioplasty transmission members are commonly connected to an extra-corporeal source of ultrasonic energy, so that it is generally necessary to deliver the ultrasonic energy over a relatively long distance, such as approximately 150 cm., to the intravascular blockage to be treated. Over such a distance, the ultrasonic energy attenuates as it passes along the length of the ultrasonic angioplasty transmission member, resulting in a loss of system efficiency, and requiring the delivery of a greater amount of acoustic energy to the ultrasonic angioplasty transmission member than actually reaches the treatment site, which can increase fatigue of the ultrasonic angioplasty transmission member and thereby increase the chances of fracturing and breakage during use, especially when the wires are bent. It is therefore desirable to provide an ultrasonic angioplasty transmission member that has a lower loss of the ultrasonic energy transmitted by the member so that lower levels of energy may be applied to the member.

In ultrasonic angioplasty techniques, accurate positioning of the ultrasound transmission member in the vasculature system to be treated requires a highly flexible ultrasonic delivery system with a low profile, especially for coronary ultrasonic angioplasty procedures, so that the catheter can more easily navigate the various vascular passages to be advanced to the occlusion. Nickel-titanium superelastic alloys have been useful in these respects as an ultrasound transmission member. Tapering or narrowing the distal end of an ultrasound transmission member to enhance flexibility of the ultrasound transmission member at its distal end is known from U.S. Pat. No. 5,304,115 (Pflueger et al.), issued Apr. 19, 1994. While such tapering or narrowing typically decreases the rigidity and improves the bendability of the ultrasound transmission member, a significant increase in amplitude of the ultrasonic energy occurs at the tapered or narrowed region. Such an increase in amplitude can cause an increased likelihood of fracturing or breakage of the ultrasound transmission member at that point during use.

Ultrasonic angioplasty transmission members that are surface hardened to reduce fracturing or breakage are disclosed in U.S. Pat. No. 5,304,115 to Pflueger et al. The ultrasound transmission members of U.S. Pat. No. 5,304,115 can be formed of one or more superelastic metal alloys, commonly known as the "shape memory alloys," such as a nickel-titanium alloy containing 50.8 atomic percent nickel, with a surface treatment of titanium nitride on the ultrasound transmission member to lower the coefficient of friction and/or increase the surface hardness of all or a portion of the ultrasound transmission member to reduce the chances of fracturing during high cycle fatigue that can occur in uncoated titanium or aluminum ultrasound transmission members.

While it is desirable to protect the outer surface of ultrasonic angioplasty transmission wires from fracturing by hardening of the outer surface, it is also desirable that such ultrasonic angioplasty transmission wires efficiently transmit sound at ultrasonic frequencies, have good tensile strength, and have a selected degree of flexibility suitable for navigating the various types of sharp bends and curves encountered in the vasculature of a patient. In general, a percutaneous transluminal angioplasty catheter may be selected to be shorter and stiffer, while a percutaneous transluminal coronary angioplasty catheter may be selected to be longer and more flexible.

Selection of a single material of the ultrasonic angioplasty transmission wire for a desired range of flexibility can at the same time affect the tensile strength, sonic properties and fatigue strength of the wire making the wire for different applications. For example, forming an ultrasonic angioplasty transmission wire of one selected ultrasound transmitting material for a desired range of flexibility of the ultrasonic angioplasty transmission wire can adversely affect the desired range of wave lengths that can be suitably transmitted in the wire, affecting the sonic transmission properties and transmission efficiency over the overall length of the catheter. In turn, forming the ultrasonic angioplasty transmission wire of one ultrasound transmitting material to improve the properties of the ultrasonic angioplasty transmission wire for transmitting a desired range of wave lengths can adversely affect the desired flexibility of the ultrasonic angioplasty transmission wire.

Hence, those skilled in the art have recognized the need for providing a structure for an ultrasonic angioplasty transmission member that allows for the use of different ultrasound transmitting materials and thicknesses to allow alteration and selection of properties of the ultrasonic angioplasty transmission member such as sonic transmission, flexibility and tensile strength, that are improved over those properties of a comparable wire formed of a single material. There is also a need for construction of an ultrasonic angioplasty transmission member that reduces attenuation of ultrasonic energy transmitted along the length of the ultrasonic angioplasty transmission member, to reduce the loss of system efficiency, and to in turn reduce the requirement for the delivery of a higher amounts of acoustical energy to the ultrasonic angioplasty transmission member, to reduce the fatigue, fracturing and breakage of the ultrasonic angioplasty transmission member that can be a consequence of high acoustical energies during use. The present invention fulfills these needs and others.

SUMMARY OF THE INVENTION

Briefly, and in general terms, the present invention is directed to an improved construction for an ultrasonic angioplasty transmission member that allows alteration of the properties of sonic transmission, flexibility, and tensile strength by providing the member with selected layering of different ultrasound transmitting materials and thicknesses of materials. In one aspect, the invention is directed to an ultrasound transmission wire for use in an ultrasonic angioplasty device, comprising an inner member of a first ultrasound transmitting material, and a first coaxial shell bonded to the inner member and formed of a second ultrasound transmitting material different from the first ultrasound transmitting material.

In more detailed aspects, the first and second ultrasound transmitting materials are selected from the group consisting essentially of stainless steel, nickel-titanium, aluminum, titanium, and multiphase alloys. Further, the first ultrasound transmitting material consists essentially of a nickel-titanium alloy and the second ultrasound transmitting material consists essentially of stainless steel. In a further aspect, the inner member comprises the core of the wire.

In yet another detailed aspect, the ultrasound transmission wire further comprises a second coaxial shell disposed over the first coaxial shell, the second coaxial shell comprising the first ultrasound transmitting material. The first and second ultrasound transmitting materials are selected from the group consisting essentially of stainless steel, nickel-titanium, aluminum, titanium, and multiphase alloys. The first ultrasound transmitting material consists essentially of a nickel-titanium alloy, and the second ultrasound transmitting material consists essentially of stainless steel.

In another detailed aspect, the invention is directed to an ultrasound transmission wire for use in an ultrasonic angioplasty device, comprising an inner member of a first ultrasound transmitting metal composition, a first coaxial tube bonded to the inner member and formed of a second ultrasound transmitting metal composition different from the first ultrasound transmitting metal composition, and a second coaxial tube bonded to the outer coaxial tube and formed of the first ultrasound transmitting metal composition.

In another main aspect, the present invention is directed to an ultrasonic angioplasty catheter device comprising an elongate flexible catheter having a proximal end, a distal end, and at least one lumen extending longitudinally therethrough, the device comprising an ultrasound transmission member extending through said lumen and having a distal end with a distal head fixed in position in the catheter for applying ultrasonic energy to an occlusive lesion, and a proximal end configured to be connected to an ultrasound generating device, wherein the distal head comprises a larger diameter distal portion positioned beyond the distal end of the catheter and a smaller diameter portion located between the distal portion and the ultrasound transmission member and extending within the catheter and wherein the ultrasound transmission member comprises a core of a first ultrasound transmitting material and a first coaxial shell bonded to the inner member and formed of a second ultrasound transmitting material different from the first ultrasound transmitting material, and a second coaxial shell disposed over the first coaxial shell, the second coaxial shell comprising the first ultrasound transmitting material.

These and other aspects and advantages of the invention will become apparent from the following detailed description and the accompanying drawings, which illustrate by way of example features of the invention.

BRIEF DESCRIPTION OF THE DRAWINGS

FIG. 5 is a sectional view of a catheter incorporating the ultrasound transmission wire shown in previous figures in an over-the-wire ("OTW") configuration, and a guide wire lumen within the distal head of the catheter; and FIG. 6 is a diagram of a rapid exchange ("RX") catheter using the ultrasound angioplasty transmission member of FIG. 1, and showing various details of the ultrasound catheter distal end.

DETAILED DESCRIPTION OF THE PREFERRED EMBODIMENTS

Figure 1:
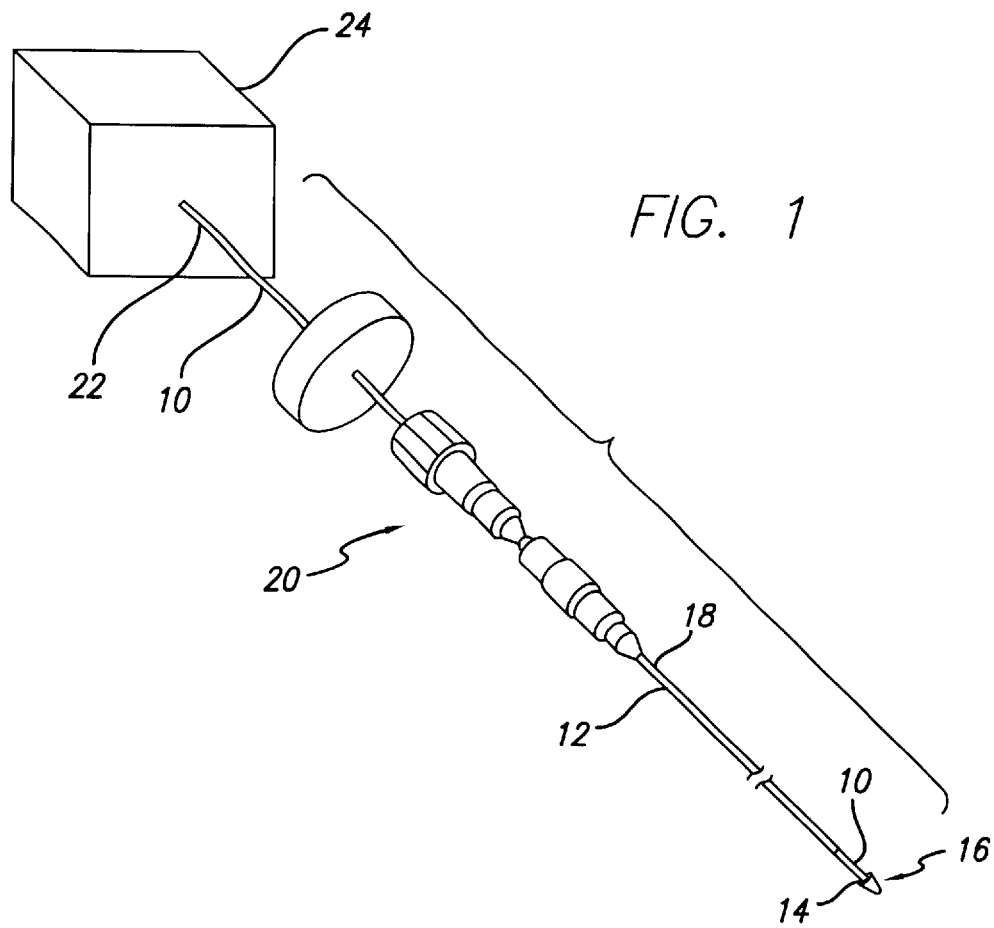
FIG. 1 is a perspective view of an ultrasonic angioplasty catheter system utilizing the ultrasonic angioplasty transmission member of the invention.

Referring to the drawings in general, the invention is embodied in an improved ultrasonic angioplasty transmission wire formed of a composite of materials constructed with an inner member and one or more outer coaxial shells or tubes formed of an ultrasound conducting material. In one embodiment, as discussed below, the layer covering the inner member is formed of a different ultrasonic conducting material from that of the inner member.

Referring to the drawings in greater detail in which like reference numerals refer to like or corresponding elements among the views, there are shown in FIG. 1 components of an ultrasonic catheter delivery system. In particular, an ultrasound transmission member or wire 10 extends longitudinally through a flexible, elongated catheter 12 having a lumen in which the ultrasound transmission member is disposed. A distal head 14 is mounted at the distal end 16 of the ultrasound transmission member for positioning in the vasculature of a patient for treatment of blockage. In accordance with the preferred embodiment, the distal head 14 is fixedly attached to the distal end of the catheter 12; however, the distal end of the catheter has been cut away in FIG. 1 so that the distal head 14 can be seen more clearly. The preferred attachment of the distal head 14 to the ultrasound transmission member 10 and the catheter 12 is shown in more detail in FIG. 5 discussed below.

The proximal end 18 of the catheter 12 is connected to a connector assembly 20, through which the ultrasound transmission member 10 passes. The proximal end 22 of the ultrasound transmission member is connected to an ultrasound transducer 24 for transmitting ultrasound energy through the ultrasound transmission member 10 to the distal head 14. Proximal connector assemblies are well known to those skilled in the art and no further details are provided here.

Figure 2:
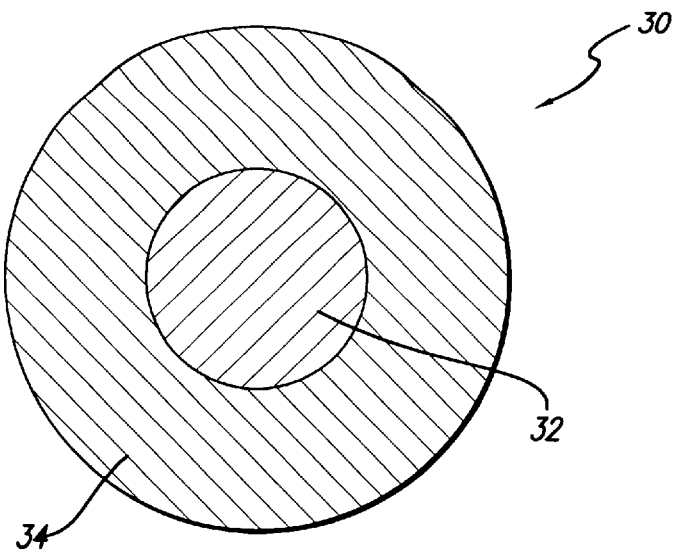
FIG. 2 is a cross-sectional view of a first embodiment of the ultrasonic angioplasty transmission wire of the invention.

With reference now to FIG. 2, which is a cross-sectional view, an ultrasonic angioplasty transmission wire 30 has a first member 32 that in this case comprises a core. The core 32 is formed of a first ultrasound transmitting material. In this embodiment, the first member is an inner member because it is surrounded by a first coaxial shell or tube 34 that is formed of a second ultrasound transmitting material that is different from that of the first ultrasound transmitting material. For example, ultrasound transmitting materials from which the first and second ultrasound conducting materials can be selected include, but are not limited to, ultrasound transmitting metals such as stainless steels, nickel-titanium alloys, aluminum, titanium, and multiphase alloys such as MP35N. Other ultrasound transmitting materials may also be suitable for use as one or more of the layers or core of the ultrasonic angioplasty transmission wire 30. The use of different ultrasound transmitting materials and thicknesses permits the alteration of and selection of properties of the ultrasonic angioplasty transmission wire, such as sonic propagation, flexibility, and tensile strength, for different applications of the ultrasonic angioplasty transmission wire, as desired.

In one presently preferred embodiment, the core 32 of the ultrasonic angioplasty transmission wire 30 is formed of a nickel-titanium alloy, and the first shell 34 or tube of the wire is formed of a thin layer of stainless steel, such as the wire currently available under the trade name Ultrasonic CoNitinol™ Wire from Surface Genesis of Sunnyvale, Calif.

The speed of sound transmission through an ultrasonic angioplasty transmission wire formed of a core of a first ultrasound transmitting material and one or more outer coaxial shells or tubes of a different ultrasound transmitting material will differ from that of a comparable wire formed of a single material, and allows alteration of the wave lengths that can be suitably propagated in the ultrasonic angioplasty transmission wire, to improve sonic propagation over the overall length of an ultrasonic angioplasty catheter.

Figure 3:
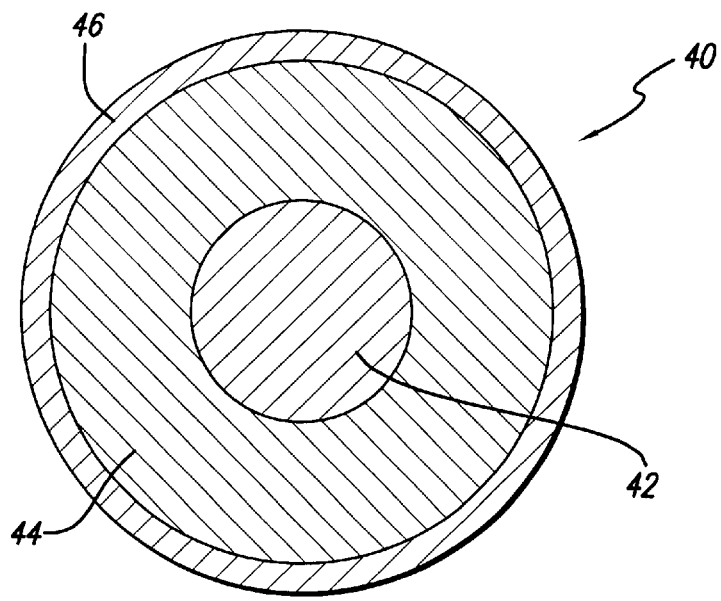
FIG. 3 is a cross-sectional view of a second embodiment of the ultrasonic angioplasty transmission wire of the invention.

In another presently preferred embodiment as illustrated in FIG. 3, an ultrasonic angioplasty transmission wire 40 has a core 42 that is formed of a first ultrasound transmitting material, a first coaxial or intermediate layer or shell or tube 44 formed of a second ultrasound transmitting material different from the first ultrasound transmitting material, and a second coaxial or outer layer or shell or tube 46 formed of the first ultrasound transmitting material again.

Ultrasound transmitting materials from which the ultrasound conducting core and one or more layers or shells or tubes can be selected include, but are not limited to, stainless steels, nickel-titanium alloys, aluminum, titanium, and multiphase alloys such as MP35N, although other ultrasound transmitting materials may also be suitable for use as one or more of the members of the ultrasonic angioplasty transmission wire.

In general, the thicker the nickel-titanium core of the wire, the better the kink resistance of the wire will be, and the thicker the stainless steel outer shell or tube, the stiffer the wire will be. Selection of materials will also affect the tensile strength, sonic properties, and fatigue strength of the wire, suitable for different applications, and generally the inner and immediately adjacent outer shells or tubes will have a different modulus of elasticity.

In each of the foregoing embodiments, the core can be formed as a solid wire or as a hollow tube of a desired thickness. Each outer coaxial tube or shell of the composite ultrasonic angioplasty transmission member need not be continuous over the entire length of the core 32 and 42. Additionally, each coaxial shell can be welded over an adjacent inner layer of the ultrasonic angioplasty transmission member, baked on, drawn, or extruded on, or otherwise deposited on and bonded to the adjacent inner layer or core.

Figure 4:
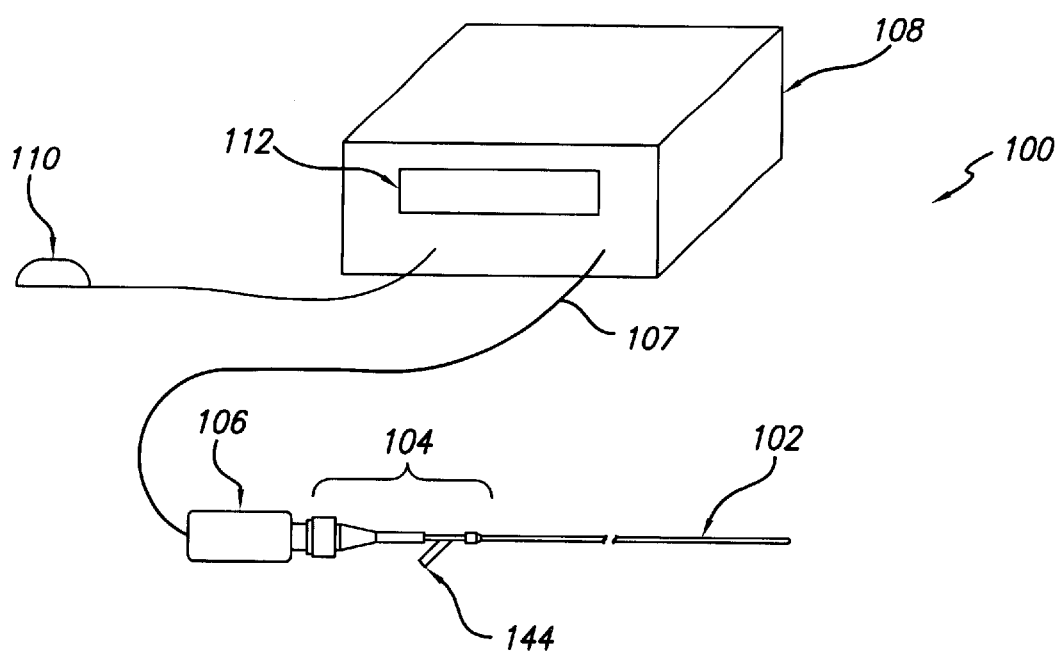
FIG. 4 is a more detailed view of a system having an ultrasonic catheter, a guide wire, an ultrasound transducer, a generator, and a foot switch.

The layout view in FIG. 4 is of an over-the-wire ultrasound catheter system 100 in which a catheter 102 has a proximal end connector assembly 104 mounted on the proximal end thereof. As used herein, the term "over-the-wire" shall refer to a catheter that has a guide wire passage lumen formed within the body of the catheter such that a flexible guide wire may be advanced through the body of the catheter and out of a guide wire passage aperture formed in the distal end of the catheter. Returning to FIG. 4, an ultrasound transducer 106 is connected to the proximal end of the proximal connector assembly 104. An ultrasound generator 108 having a foot-actuated on/off switch 110 is operatively connected to the ultrasound transducer 106 through an electrical cable 107 so as to send ultrasonic energy through the ultrasound catheter 102, when desired. The generator 108 includes a display 112 that presents certain information about the ultrasonic energy application process.

The distal end of the catheter 102 may include a dilatation balloon, a stent, or other apparatus depending on the configuration selected and is configured to be percutaneously inserted into a body vascular system and through tortuous body lumina to a desired location within the body vascular system. The catheter 102 includes an ultrasound transmission wire (not shown) as described above.

Turning now to FIG. 5, a sectional view of part of the catheter 102 is shown. An ultrasound transmission member 114 formed of a core of one ultrasonic transmission material and at least one shell of a second ultrasonic transmission material different from the first material includes tapering 116 for amplification at its distal end. The taper 116 terminates in a reduced diameter section 118 of the ultrasound transmission member 114. Because the reduced diameter distal portion 118 of the ultrasound transmission member 114 is of smaller cross-sectional diameter and less mass, it is more flexible and less rigid than the proximal portion thereof. In the embodiment of the catheter 102 shown in FIG. 5, the outer diameter of the distal portion 120 of the catheter is also reduced to coincide with the reduced diameter distal portion 116, 118 of the ultrasound transmission member 114, and also will exhibit less rigidity and greater flexibility than the remainder of the catheter body.

The present embodiment further includes an optional improvement to the ultrasound transmission member 114, said improvement comprising the disposition of a low friction coating or jacket 122 on the outer surface of all or a portion of the ultrasound transmission member 114. The low friction coating or jacket 122 may be disposed on the outer surface of the ultrasound transmission member so as to completely cover the ultrasound transmission member along its entire length, or along a discrete region or regions thereof. Such coating or jacket 122 may comprise a layer of low friction polymer material such as polytetrafluoroethylene (ptfe) (Teflon™ Dupont, Inc., Wilmington, Del.) or other plastic materials such as polyethylene. The coating or jacket 122 may be applied as a liquid and subsequently allowed to cure or harden on the surface of the ultrasound transmission member 114. Alternatively, the coating or jacket 122 may be in the form of an elongate tube slidably disposable over the outer surface of the ultrasound transmission member. Such coating or jacket 122 serves to prevent or diminish friction between the outer surface of the ultrasound transmission member 114 and the adjacent structures of the catheter or proximal end connector assembly 104 through which the ultrasound transmission member 114 extends.

A distal head 124 is firmly bonded, attached, or connected to the catheter body 126 such that the distal head is prevented from undergoing longitudinal or transverse movement separate from or relative to the catheter body. Additionally, such affixation of the distal head to the catheter body increases the conveyance of ultrasound energy into the distal portion of the catheter body 126, thereby resulting in enhanced cavitation effects created by the distal portion of the catheter body. Such bonding connection or attachment of the distal head 124 to the catheter body 126 may be accomplished by any suitable means. One means of attaching the distal head 124 to the catheter body 126 is through the use of an adhesive.

In the embodiment shown in FIG. 5, the adhesive is applied to the neck portion 128 of the distal head 124 prior to insertion thereof into the distal end of the lumen 130 of the catheter body 126. The adhesive may comprise any suitable adhesive, such as cyanoacrylate (e.g. Loctite™, Loctite Corp., Ontario, CANADA or Dron Alpha™, Borden, Inc., Columbus, Ohio) or polyurethane (e.g. Dymax™, Dymax Engineering Adhesive, Torrington, Conn.) to firmly bond and attach the distal head 124 to the catheter body 126.

The distal head 124 may be formed of any suitable rigid material such as metal or plastic. In devices wherein the distal head is formed of plastic, the surrounding plastic catheter body 126 may be thoroughly welded, heat sealed, or solvent welded to the plastic distal head 124, in accordance with the types of plastics employed.

In the alternative to the use of adhesives, various mechanical or frictional connectors, such as screw threads, lugs or other surface modifications formed on the neck portion 128 of the distal head 124, may be utilized to hold the distal head 124 in a fixed position relative to the catheter body 126. In such embodiments, corresponding grooves, detents or surface modifications may also be formed in the surrounding inner wall of the catheter body 126 so as to cooperate with any such threads, lugs or other surface modifications formed on the opposing surface of the distal head 124. Such threads, lugs or other surface modifications will be configured and constructed so as to mechanically or frictionally hold the distal head 124 in fixed position relative to the catheter body 126.

The distal head 124 is preferably formed of radio dense material so as to be easily discernable by radiographic means. Accordingly, the distal head 124 may preferably be formed of metal or, alternatively, may be formed of plastic, ceramic or rubber materials, optionally having one or more radio dense markers fixed thereto or formed therein. For example, the distal head 124 may be molded of plastic such as acrylonitrile-butadiene-styrene (ABS) and one or more metallic foil strips or other radio opaque markers may be affixed to such plastic distal head 124 in order to impart sufficient radio density to permit the distal head to be readily located by radiographic means. Additionally, in embodiments wherein the distal head is formed of molded plastic or other non-metallic material, a quantity of radio dense filler such as powdered bismuth or $BaSO_4$ may be disposed within the plastic or other non-metallic material of which the distal head is formed so as to impart enhanced radio density to the distal head.

The ultrasound transmission member 114 is tapered outward 132 at its most distal extreme 134 to a size that fits within a cavity 136 formed in the distal head 124. Although this outward taper attenuates the ultrasonic energy somewhat, it results in greater stability of the ultrasound transmission member 114 at the distal end because there is more surface area provided for adhesive attachment to the distal head and less likelihood of breakage at the attachment point.

Also shown in FIG. 5 is a guide wire 138 disposed in a guide wire aperture 140 formed in the distal head 124. The catheter body may include a separate guide wire lumen 142 within which the guide wire is disposed thus forming an over-the-wire (OTW) catheter arrangement. The guide wire may be introduced and retracted from the catheter body through a side arm 144 shown in FIG. 4.

Another feature of the catheter 12 is shown in FIG. 5. At the distal end 120, two tubular members are joined to result in the catheter shaft. In particular, a first tubular member 166 is used for the proximal and center sections of the catheter shaft while a second tubular member 168 is used for the distal section 120. As shown, the second, distal, tubular member 168 overlaps the first tubular member. The two members may be held together with adhesive. Such configuration to the catheter enables more cost effective manufacturing techniques as well as greater accuracy in manufacturing the catheter.

Turning now to FIG. 6, a rapid exchange or "RX" embodiment of a catheter is shown. In this embodiment, the catheter body 180 may be provided with a distal guide wire passage tube 182 positioned within the inner bore or lumen 184 of the catheter body 180 and extending from a guide wire re-entry aperture 186 to the guide wire passage aperture 188 formed in the distal head 192 of the device. As such, the proximal end member (not shown) of a guide wire 190 may be inserted into the distal head 192 of the catheter body 180 through the guide wire passage aperture 188 and subsequently disposed in a proximal direction through the guide wire lumen 184 of the guide wire tube 182 to a point where the proximal end of the guide wire 190 emerges from the guide wire entry/re-entry aperture 186. After emerging from the guide were entry/re-entry aperture 186, the proximal portion (not shown) of the guide wire 190 may extend and/or reside adjacent the outer surface of the proximal portion (not shown) of the catheter body 180. The catheter body 180 and the guide wire 190 may then be distally and/or proximally repositioned, relative to one another, during the procedure. Also, if desired, the guide wire 190 may be fully withdrawn and extracted by pulling the guide wire in a proximal direction such that the distal tip 194 of the guide wire is pulled through the distal head 192, through the guide wire passage tube 182, and out of the guide wire entry/reentry aperture 186, and the guide wire 190 is subsequently fully withdrawn from the catheter body 180, leaving only the ultrasound catheter in place in the patient.

The distal portion of the catheter shown in FIG. 6 contains many of the same elements shown in other figures. In particular, the distal head 192 is fixedly attached to the catheter body 180 through adhesive or other means. An ultrasound angioplasty transmission member 196 such as that shown in FIGS. 2 and 3 above is attached to the distal head 192 and has a stepped down length 198 with a conical transition area 200. An enlarged area 202 of the distal portion is used to accommodate the additional guide wire tube 182 in this RX embodiment.

Although embodiments shown and described herein include OTW and RX catheters, other embodiments are possible that include combinations or hybrids of OTW and RX. As is apparent, an RX catheter system is also easily used with the ultrasound angioplasty transmission member described and shown.

It will be apparent from the foregoing that while particular forms of the invention have been illustrated and described, various modifications can be made without departing from the spirit and scope of the invention. Accordingly, it is not intended that the invention be limited, except as by the appended claims.

What is claimed is:

1. An ultrasonic angioplasty catheter device comprising an elongate flexible catheter having a proximal end, a distal end, and at least one lumen extending longitudinally therethrough, the device comprising:

an ultrasound transmission member extending through said lumen in a fixed position within the catheter lumen and having a distal end with a head for applying ultrasonic energy to an occlusive lesion, and a proximal end configured to be connected to an ultrasound generating device, the distal head being positioned on the distal end of said ultrasound transmission member such that the distal head extends beyond the distal end of the catheter;

wherein the ultrasound transmission member comprises an inner member of a first ultrasound transmitting material and a first coaxial shell bonded to the inner member and formed of a second ultrasound transmitting material different from the first ultrasound transmitting material.

2. The ultrasonic angioplasty catheter device of claim 1 wherein the distal head comprises a larger diameter distal portion positioned beyond the distal end of the catheter and a smaller diameter portion located between the distal portion and the ultrasound transmission member and extending within the catheter.

3. The ultrasonic angioplasty catheter device of claim 2 wherein the distal head is fixed in position in the catheter.

4. The ultrasonic angioplasty catheter device of claim 1 wherein the ultrasound transmission member has a distal portion with at least one amplification region of reduced cross-sectional diameter where transverse vibration of ultrasonic energy transmitted by the ultrasound transmission member is amplified.

5. The ultrasonic angioplasty catheter device of claim 1 wherein the first and second ultrasound transmitting materials are selected from the group consisting essentially of stainless steel, nickel-titanium, aluminum, titanium, and multiphase alloys.

6. The ultrasonic angioplasty catheter device of claim 1 wherein the first ultrasound transmitting material consists essentially of a nickel-titanium alloy.

7. The ultrasonic angioplasty catheter device of claim 1 wherein the second ultrasound transmitting material consists essentially of stainless steel.

8. The ultrasonic angioplasty catheter device of claim 1 further comprising a second coaxial shell disposed over the first coaxial shell, the second coaxial shell comprising the first ultrasound transmitting material.

9. The ultrasonic angioplasty catheter device of claim 8 wherein the inner member comprises the core of the wire.

10. The ultrasonic angioplasty catheter device of claim 8 wherein the ultrasound transmission member has a smaller diameter towards its distal end and increases to a larger diameter towards its proximal end.

11. The ultrasonic angioplasty catheter device of claim 1 wherein the distal head comprises a guide wire aperture to permit passage of a guide wire therethrough.

* * * * *

UNITED STATES PATENT AND TRADEMARK OFFICE
CERTIFICATE OF CORRECTION

PATENT NO.    : 6,589,253 B1
DATED         : July 8, 2003
INVENTOR(S)   : Wayne E. Cornish et al.

It is certified that error appears in the above-identified patent and that said Letters Patent is hereby corrected as shown below:

<u>Column 10,</u>
Line 25, change "8", to read -- 9 --.

Signed and Sealed this

Twenty-seventh Day of January, 2004

JON W. DUDAS
*Acting Director of the United States Patent and Trademark Office*